(12) United States Patent
Olivieri et al.

(10) Patent No.: US 6,716,227 B2
(45) Date of Patent: Apr. 6, 2004

(54) APPARATUS AND METHOD FOR CORNEAL SURGERY

(75) Inventors: Luigi Olivieri, Via G. M. Paolini, 12, S. Benedetto del Tronto AP (IT), 63039; Franco Zocchi, Rome (IT); Italo Cantera, Rome (IT)

(73) Assignees: Meditekno S.r.l., Rome (IT); Luigi Olivieri, S. Benedetto del Tronto (IT)

( * ) Notice: Subject to any disclaimer, the term of this patent is extended or adjusted under 35 U.S.C. 154(b) by 0 days.

(21) Appl. No.: 09/949,208

(22) Filed: Sep. 7, 2001

(65) Prior Publication Data

US 2002/0077699 A1 Jun. 20, 2002

(30) Foreign Application Priority Data

Sep. 8, 2000 (EP) .............................. 00830612

(51) Int. Cl.[7] .................................................. A61F 9/00
(52) U.S. Cl. ..................................................... 606/166
(58) Field of Search .......................... 606/166, 167, 606/161, 180, 172

(56) References Cited

U.S. PATENT DOCUMENTS

| | | | | |
|---|---|---|---|---|
| 2,480,737 A | * | 8/1949 | Jean-Edward | 606/166 |
| 4,205,682 A | * | 6/1980 | Crock et al. | 606/166 |
| 4,423,728 A | * | 1/1984 | Lieberman | 606/166 |
| 4,429,696 A | * | 2/1984 | Hanna | 606/166 |
| 4,815,463 A | * | 3/1989 | Hanna | 606/166 |
| 5,290,301 A | * | 3/1994 | Lieberman | 606/166 |
| 5,626,594 A | * | 5/1997 | Smith | 606/166 |
| 5,964,776 A | * | 10/1999 | Peyman | 606/166 |
| 6,458,141 B1 | * | 10/2002 | Peyman | 606/166 |

* cited by examiner

*Primary Examiner*—Michael J. Milano
*Assistant Examiner*—D. Jacob Davis
(74) *Attorney, Agent, or Firm*—Leffert, Jay & Polglaze, P.A.

(57) ABSTRACT

Apparatus and method for corneal surgery, apt to increase the accuracy of the surgical interventions, comprising a chassis, apt to be placed onto the eyeball for the centration with respect to the eyeball of the apparatus itself; at least one surgical device, apt to operate onto the corneal tissue, insertable in the apparatus; a cylindrical dowel for positioning the surgical device, movable with respect to the chassis, apt to be handled by a user for bringing the surgical device in an operative position; and a shaped body for moving the surgical device, also movable with respect to the chassis, apt to be handled by a user to actuate the surgical device, in the operative position, according to a pre-set actuating path (FIG. 1).

17 Claims, 5 Drawing Sheets

APPARATUS AND METHOD FOR CORNEAL SURGERY

FIELD OF THE INVENTION

The present invention relates to an apparatus for corneal surgery. In particular, it relates to an apparatus comprising a chassis, apt to be placed onto the eyeball for the centration of said apparatus with respect to the eyeball.

BACKGROUND OF THE INVENTION

Corneal surgery operations envisage the caging of the cornea, and the actuation of a surgical device apt to operate thereon.

In particular, corneal transplant surgery operations require carrying out a cutting onto the patient's damaged cornea, in order to remove a button therefrom. Thus, a so-called <<bed>> apt to receive a matching donor corneal portion is obtained. The donor portion is placed within the bed itself and sutured to the walls thereof. Presently, said removal of a button from the patient's cornea is carried out by a substantially punch-shaped surgical cutter, usually hand-actuated by a surgeon. Such removal generally concerns the entire corneal thickness, even for mere superficial lesions.

Recently, the introduction in the ophthalmologic field of the excimer laser, which vaporises tissues by breaking their molecular bonds, has allowed to improve the accuracy of corneal surgery techniques, and in particular of the so-called lamellar corneal surgery. According to these latter ones, the surgeon operates only on a layer of the damaged cornea, rather than over the entire depth thereof.

In particular, the excimer laser enables an accurate sculpturing the donated corneal portion, in order to better adapt it to the type and depth of the patient's corneal lesion, as well as to precisely calculate the thickness of the bed for housing such donated portion, removing extremely regular corneal layers.

The above-described surgical instruments and the related surgical techniques have several relevant drawbacks.

The main drawback lies in the fact that the instruments used to date, being hand-actuated, allow to obtain only a reduced surgical accuracy.

Therefore, in corneal transplant surgery the housing of the donated corneal portion within the related bed is not optimal, and the advantages potentially associated with the use of the excimer laser are not fully exploited.

OBJECT AND SUMMARY OF THE INVENTION

The technical problem underlying the present invention is that of providing an apparatus for corneal surgery allowing to overcome the drawbacks hereto mentioned with reference to the known art.

This problem is solved by an apparatus for corneal surgery, comprising:

- a chassis, apt to be placed onto the eyeball for centrating said apparatus with respect to the eyeball;
- at least one surgical device, apt to operate onto corneal tissue, insertable in said apparatus;
- surgical device positioning means, movable with respect to said chassis, apt to be handled by a user for bringing said at least one surgical device in an operative position; and
- surgical device moving means, also movable with respect to said chassis, apt to be handled by the user for actuating said at least one surgical device, in said operative position, according to a pre-set actuating path.

The present invention also provides a surgical method for performing a corneal transplant, comprising the steps of:

- forming a bed of a desired thickness into the patient's cornea;
- penetrating the side wall of said bed for a desired extension by at least one cutting tool, according to a penetration direction transverse to an eyeball axis;
- cutting an incision, by said cutting tool, of a substantially circular profile so that a flap of corneal tissue is obtained, a pocket being defined between said flap and the underlying cornea; and
- resting a corneal portion to be transplanted into said bed, so that said flap partially overlaps said corneal portion.

The present invention provides several relevant advantages. The main advantage lies in the fact that in the apparatus of the invention specific means are provided for positioning the surgical device and for actuating it, which allow to carry out extremely accurate operations.

Other advantages, features and operation modes of the present invention will be made evident in the following detailed description of some embodiments thereof, given by way of example and not for limitative purposes. Reference will be made to the figures of the annexed drawings.

DETAILED DESCRIPTION

Figure 1:
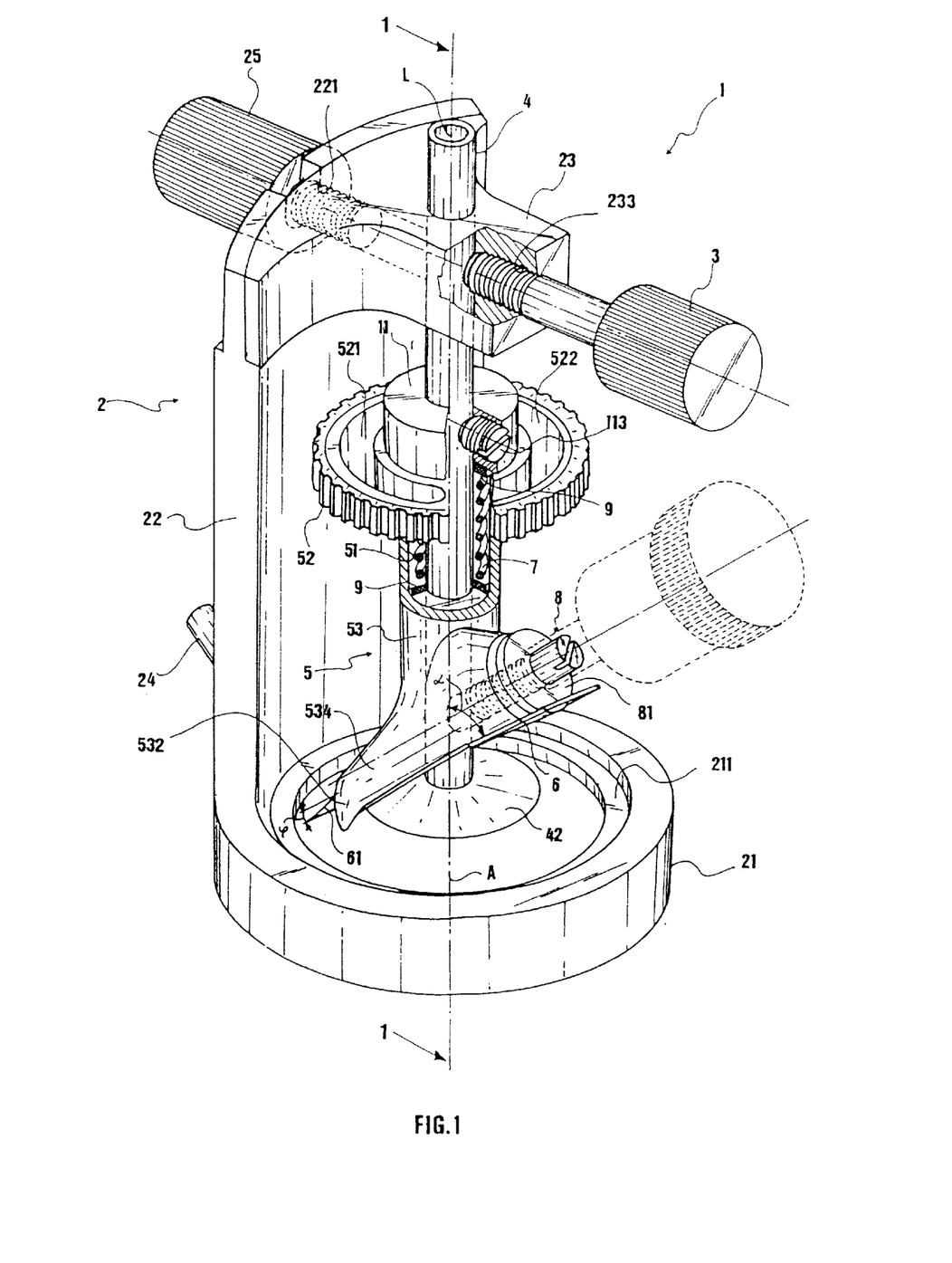
FIG. 1 is a perspective view of a first embodiment of the apparatus according to the present invention.
Figure 2:
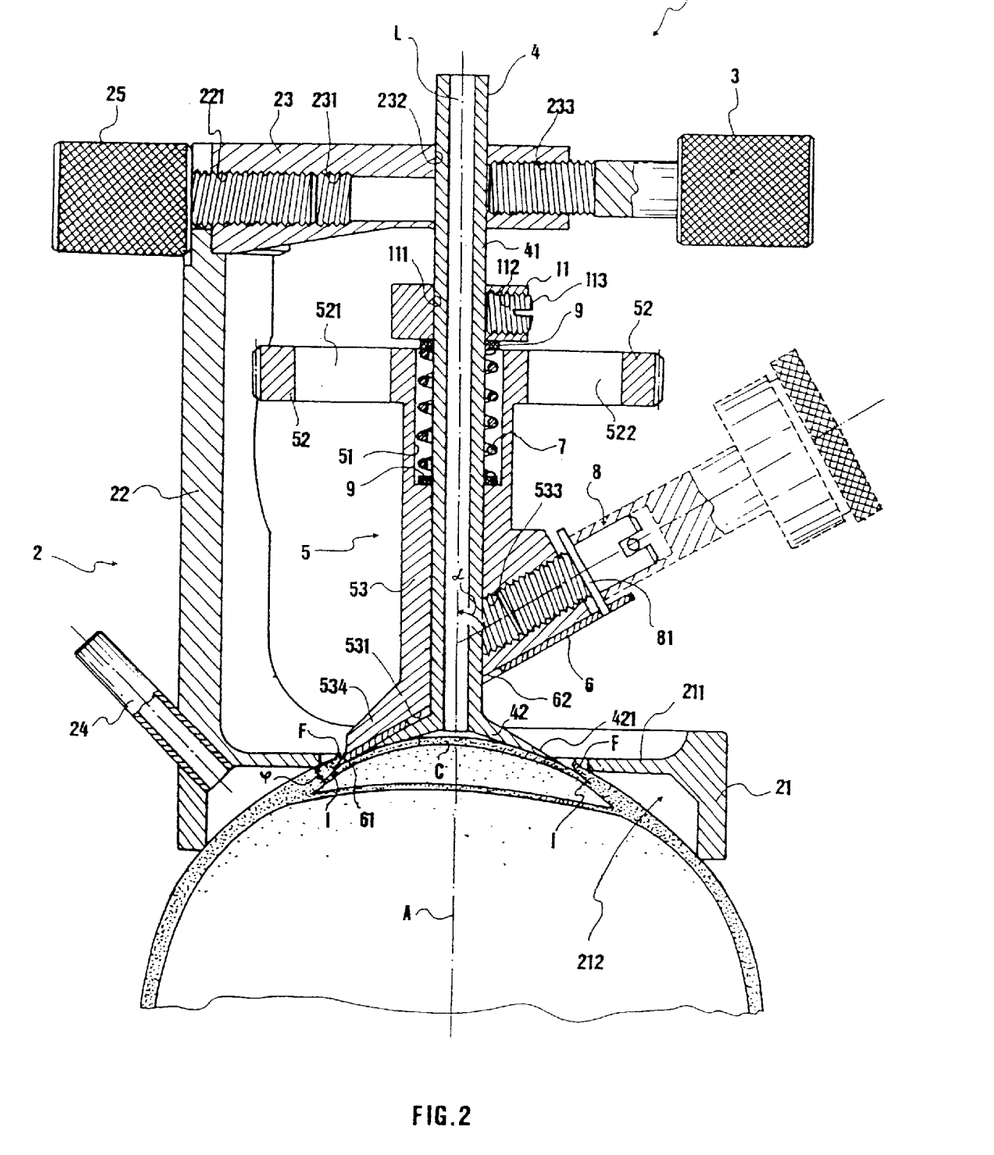
FIG. 2 is a sectional view of the apparatus of FIG. 1 taken along line A—A of the latter Figure, in an operative condition during lamellar corneal transplant surgery.

FIGS. 1 and 2 relate to a first embodiment of an apparatus for corneal surgery, in particular a cutting apparatus, globally indicated with 1 and depicted in a fully assembled condition.

With reference to said Figures, according to the invention the apparatus 1 comprises a chassis, globally indicated with 2.

In the present embodiment, the chassis 2 in turn comprises, bottomwise, a substantially horizontal annular structure 21, apt to be placed during the corneal surgery operation onto the eyeball, for centrating the apparatus 1 itself with respect to the eyeball and for caging the cornea, indicated with C in FIG. 2. In particular, in FIG. 2 the axis of the eyeball is indicated with A. The chassis 2 further comprises a shaped vertical rod 22, developing sideways to the annular structure 21 and integral therewith. The chassis 2 further provides a transverse rod 23, reversibly connected to the vertical rod 22. By virtue of such reversible connection, the chassis 2 of the present embodiment is disassemblable.

Topwise, the annular structure 21 ends in an annular edge 211, protruding internally to the structure itself. The latter defines in its interior a circular room, globally indicated with 212, apt to receive the exposed eyeball portion. Topwise, at the annular edge 211, such room narrows, anyhow allowing the reception of the eyeball bearing the cornea C.

The chassis 2 is crossed, at the annular structure 21, by one or more suction ducts 24, for facilitating the adhesion of the eyeball to the apparatus 1 during the surgical intervention. Therefore, the ducts 24 can be connected, externally to the apparatus 1, to suction devices of the conventional type (not shown in the Figures).

The vertical rod 22 has, at a top end thereof, a U-shaped seat 221, apt to receive a connecting member 25. The latter is apt to reversibly connect the two rods 22 and 23, and can therefore be handled by a user, typically a surgeon, for assembling/disassembling the chassis 2.

In a plan view, the transverse rod 23 is substantially T-shaped, and it is arranged orthogonally to the vertical rod 22 when the apparatus 1 is assembled. Also the transverse rod 23 has a connecting seat 231, in particular a threaded hole, which develops parallelly to the longitudinal axis of the "T" and is apt to receive said connecting member 25.

Furthermore, the transverse rod 23 has a cannula seat 232, in particular a through hole, developing in a direction orthogonal to the plane of the "T" and apt to allow the passage through the rod 23 itself of a cannula 4, that will be detailed hereinafter. Such cannula seat 232 is axial to the annular structure 21 of the chassis 2.

The transverse rod 23 also has, at the opposite side of the cannula seat 232 with respect to the connection seat 231, a further threaded seat 233, also having an axis substantially parallel to the longitudinal axis of the "T", apt to receive a cannula locking member 3. The latter is apt to engage the seat 233 until abutting the outer side wall of the cannula 4, for locking the cannula itself with respect to the chassis 2.

In the present embodiment, the connecting member 25 and the cannula locking member 3 are each a screw for ophthalmologic use, comprising a threaded body and a handling head. A person skilled in the art will understand that, compared to the usual screws for generic mechanical use, the screws for ophthalmologic use as those at issue are specifically designed in terms of dimensions, weight and machining for precision applications. In particular, said handling head has dimensions relatively greater with respect to those of the screws of common use in order to facilitate the gripping thereof by a user, and in particular by a surgeon in an operating theatre.

According to the invention, the apparatus 1 further comprises surgical device moving means 5. When the apparatus is in an assembled condition, such means 5 is constrained to the chassis 2 at the above-mentioned cannula 4 and movable with respect to it, for actuating according to a pre-set actuating path a surgical device 6 apt to operate onto the corneal tissue. In the present embodiment, such surgical device is a blade, it also indicated with 6, apt to penetrate the corneal tissue and actuatable according to an actuating path of substantially circular profile. Such blade 6 will be detailed later on.

In the present embodiment, the moving means 5 comprises a shaped body, it also indicated with 5, having a longitudinal axis indicated with L in FIG. 2. As it will be made evident hereinafter, with reference to the operation modes of the apparatus 1, such longitudinal axis L coincides, during cutting, with the eyeball axis A.

Along the longitudinal axis L a through hole 51 which concerns the entire longitudinal extension of the shaped body 5 develops, apt to rotatably receive said cannula 4. The hole 51 has a top portion of greater diameter, apt to receive axial locking means that will be detailed later on.

Furthermore, topwise the shaped body 5 provides an actuation head 52, apt to be gripped by the surgeon for actuating the above-mentioned blade 6. Onto the actuation head 52, two substantially rounded C-shaped openings 52 are formed. In particular, the head 52 has a first visualization opening 521, of greater extension, for allowing the surgeon to visualize the blade 6 during the cutting of the cornea, as it will hereinafter be evident, with reference to the operation modes of the apparatus 1. Moreover, the actuation head 52 has a second lightening opening 522, of lesser extension with respect to the first opening.

The shaped body 5 continues in a substantially tubular portion 52, and, bottomwise thereto, in a surgical device guiding and positioning portion 53. The latter has, sideways, a slanting threaded seat 533, the moving means 5 being constrained thereat to surgical device positioning means 8, which will be disclosed hereinafter. Such slanting seat 533 actually has an axis slanting with respect to the longitudinal axis L of the shaped body 5. In order to attain an optimal cutting, said slant, which hereinafter will be referred to as positioning slant and which is indicated with an angle $\alpha$ in FIG. 2, is preferably comprised in a range of about 10÷30 degrees.

Opposite to such seat 533, the guiding and positioning portion 53 has a protruding appendix 534, it also slanting, apt to maintain, during the cutting, the blade 6 in contact with the cannula 4.

The portion 53 then ends with a slanting face 531, substantially parallel to the seat 533 of the positioning means 8, apt to abut the blade 6. Such slanting face 531 has, at each of two opposite side edges thereof, an abutting edge 532, shown in FIG. 1, for maintaining in position the blade 6 during cutting.

As abovementioned, the apparatus 1 also comprises axial locking means, and in particular a counteracting elastic member 7 and an axial locking member 11.

In the present embodiment, the counteracting elastic member 7 is a helical extension-compression spring, housed within the top portion of greater diameter of the hole 51 of the shaped body 5. In particular, the bottom end coil thereof is abutted on a bottom abutting edge of said portion, with the interposition of a bottom washer 9. The latter is made in a material of low friction coefficient, e.g., Teflon. Topwise, instead, the spring 7 is apt to abut said axial locking member 11, with the interposition of a top washer analogous to the abovementioned one, and it also indicated with 9.

The axial locking member 11 has a central cannula seat 111, apt to allow the passage of the cannula 4 through the member itself. Further, the member 11 has a threaded side seat 112, apt to receive a screw for ophtalmological use 113 of the abovedisclosed type, for locking sideways the member 11 itself onto the cannula 4. Therefore, as it will be better understood hereinafter, when the apparatus 1 is in an assembled condition, the axial locking member 11 axially locks the shaped body 5, in order to avoid a possible lifting of the latter with respect to the eyeball during cutting.

The abovementioned positioning means 8 is apt to position the blade 6 in an operative position wherein the blade 6 incises the cornea C. In the present embodiment, such means 8 comprises a cylindrical threaded dowel, it also indicated with 8, apt to be screwed within the slanting seat 533. Therefore, in said operative position the blade 6 has the abovementioned slant α with respect to the axis A of the eyeball.

Said dowel 8 has a protruding circular tongue 81, implementing reversible engagement means for retaining the blade 6, as it will hereinafter be illustrated. Such tongue 81 also constitutes a safety stop for the advancing of the threaded dowel 8 within its seat 533, i.e. for limiting the depth and the radial extension of the penetration of the blade 6 into the eyeball.

As it will be better understood with reference to the operation modes of the apparatus 1, said screw thread coupling between the positioning means 8 and the seat 533 also implements a system for the adjustment of the position of the surgical device with respect to the eyeball. In particular, such system allows an adjustment of the depth and of the radial extension of the penetration of the blade 6 into the patient's cornea C.

The means 8 may be handled by reversibly connecting it to handling means (schematically shown as hatched in FIG. 2) such as a hand grip or the like, for facilitating the actuation thereof by the surgeon.

The cannula 4 is substantially shaped as an inverted funnel. Therefore, it provides a substantially tubular top portion 41 and a bottom surgical device guiding portion 42, shaped as a conical cup, apt to be placed onto the eyeball at the cornea C. The side wall of this latter portion, indicated with 421, is apt to allow the sliding thereon of the blade 6, guiding it to follow the abovementioned substantially circular path.

Also the top end of the cannula 4 can be connected to conventional suction means, for favouring the adhesion of the surgical device guiding portion 42 to the cornea C.

When the apparatus 1 is in an assembled condition, the tubular portion 41 of the cannula 4 is arranged through the cannula seat 232 of the chassis 2, the central cannula seat 111 of the axial locking member 11, the hole 51 of the shaped body 5, through the helical spring 7, and a cannula hole 62 formed into the blade 6. In such assembled configuration, the cannula 4 can be made integral to the chassis 2 by actuating the cannula locking member 3. Thus, also the moving means 5 and the positioning means 8 are constrained to the chassis 2. Moreover, the axial locking member 11 can be made integral to the cannula 4 itself by actuating the abovementioned screw.

Figure 3:
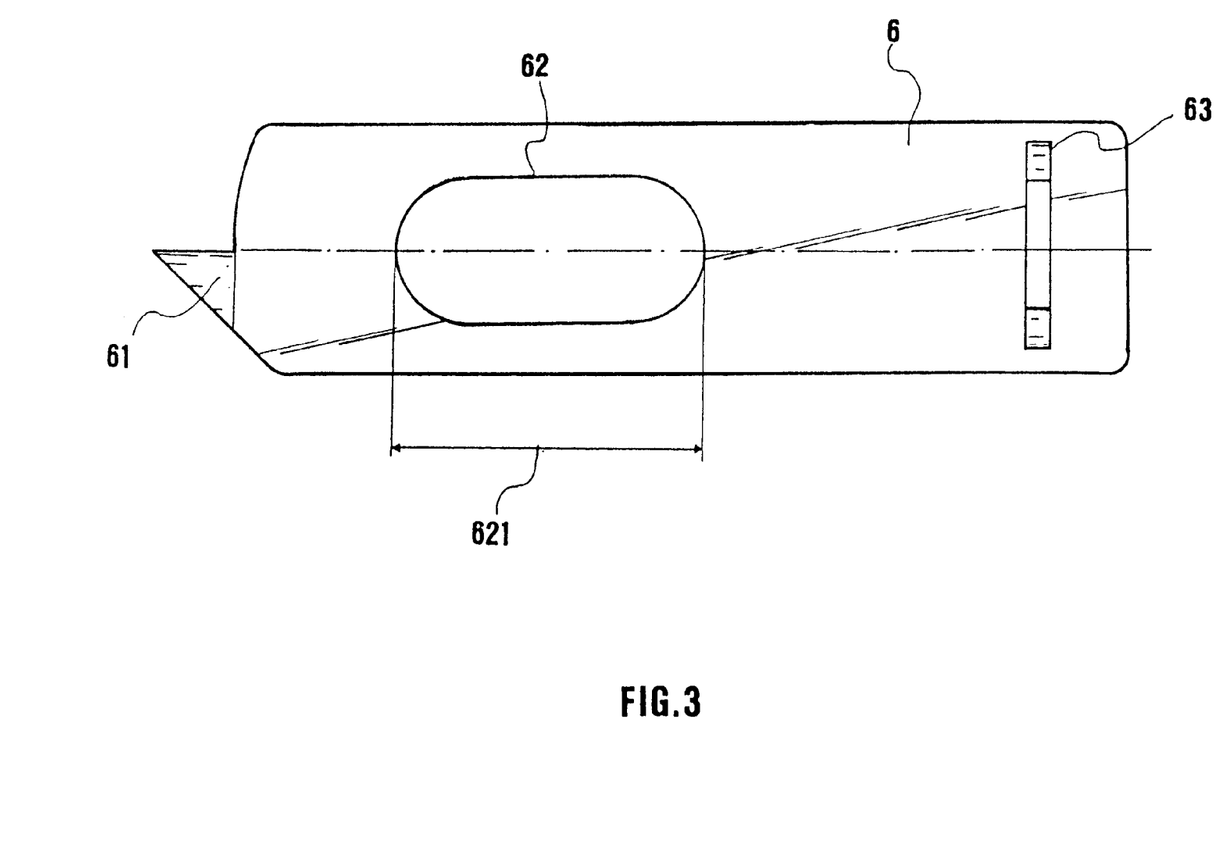
FIG. 3 is a plan view of a surgical device of the apparatus of FIG. 1.

With reference now also to FIG. 3, the blade 6 is substantially flat, and in a plan view it has a substantially rectangular shape. In particular, always in a plan view, the blade 6 has a transversal dimension substantially equal to the distance between the two abutting edges 532 of the slanting face 531.

Frontwise, the blade 6 provides a protruding side cutting tooth 61. In a plan view, the latter is shaped substantially as a right-angled triangle, and, it being sharp, the thickness thereof tapers from the bottom to the top. Therefore, in a front view it has a cutting-edge angle, indicated with φ in FIG. 2. Preferably, for an optimal cutting, such angle φ equals about 15°.

The blade 6 has, near to the tooth 61, said cannula hole 62, for the passage of the cannula 4. Such cannula hole 62 has an elongated shape and, in particular, a longitudinal dimension, indicated with a reference arrow 621 in FIG. 3, greater than that strictly necessary for the passage of the cannula 4. This is due to the need to allow a translation of the blade 6 onto the slanting face 531 of the shaped body 5 during the positioning of the blade itself in said operative position, as well as an adjustment of the position of the blade 6 with respect to the eyeball.

Moreover, rearwise the blade 6 has an engagement seat 63 for rotatably and reversibly receiving the tongue 81 of the positioning dowel 8. Therefore, the tongue 81 and the seat 63 thereof implement the above-mentioned engaging means, by which the blade 6 is constrained to translate integrally to the dowel 8 in a direction parallel to the axis of the seat 63. According to a variant embodiment, further engaging means may be provided for holding the blade 6, like, e.g., a pin applied at the slanting face 531 of the moving means 5.

All the heretodisclosed components, of course apart the washers 9, are preferably made of stainless steel.

It will at this point be appreciated that, by virtue of its modular structure, the apparatus 1 may be provided to the user in a disassembled condition. In such a condition, the apparatus 1 has reduced dimensions and thus may effectively be put away in a protective case.

The operation mode of the apparatus of the invention will hereinafter be illustrated with reference to FIG. 2. In particular, the use of the apparatus 1 will be illustrated with reference to a corneal lamellar transplant intervention.

Firstly, an eyelid retractor is applied onto the patient's eye in order to cage the eyelids thereof, as it will be well-known to a person skilled in the art.

Then, the chassis 2 is placed onto the eyeball at the annular structure 21 thereof, and centrated thereon in such a manner that the longitudinal axis L of the apparatus 1 coincides with the axis A of the eyeball itself. Then the suction means, e.g. of a pump type, may be connected to the ducts 24, in order to ensure the adhesion of the eyeball to the annular structure 21.

At this point, the surgeon can use an excimer laser for forming a bed B of a desired thickness into the patient's cornea C.

Then, the surgeon can end the assembling of the apparatus 1. To this end, firstly the surgeon connects the positioning means 8 to the moving means 5, by the related screw-thread coupling.

Then, the blade 6 can be inserted into the apparatus 1, constraining the former to the positioning means 8, and in particular bringing into engagement the circular tongue 81 of means 8 within the engagement seat 63. In this condition, the blade 6 can be held in abutment onto the slanting face 531 of the shaped body 5, and it is housed between the two abutting edges 532 thereof.

Then, the tubular portion 41 of the cannula 4 may be inserted, from the bottom, through the blade 6, the hole 51 of the shaped body 5, the top washer 9 and the axial locking member 11, until the protruding side appendix 534 of the shaped body 5, with the interposition of the blade 6, abuts the side wall 421 of the cup-shaped portion 42.

If, in this condition, the tooth 61 of the blade 6 protrudes behind the side wall 421 of the cannula 4, the positioning means 8 may be actuated, in order to move the blade 6 backward until the tooth 61 is shielded, bottomwise, by said side wall 421.

Then, the transverse rod 23 can be inserted onto the tubular portion 41 of the cannula 4, passing the latter through the cannula seat 232. Then, the transverse rod 23 itself can be connected to the vertical rod 22 by the connecting member 25. Then, the cannula 4 may temporarily be locked to the transverse rod 23 by the cannula locking member 3.

In this assembled condition, the longitudinal axis L of the moving means 5 coincides with the longitudinal axis of the cannula 4.

It will be appreciated that the assembly of the apparatus 1 can simply and quickly be carried out in the operating theatre itself.

Then, the cannula locking member 3 is moved back within the seat 233 thereof for releasing the cannula 4, so that the latter may gravity slide until it rests onto the cornea C. Concomitantly, the shaped body 5 and the blade 6 integral thereto are brought into abutment onto the cup-shaped portion 42 of the cannula 4.

Once in such intervention position, the cannula 4 is again locked to the chassis 2 by the locking member 3. Moreover, the axial locking member 11 is locked onto the cannula 4 by the screw 113 inserted in the seat 112, slightly compressing the spring 7.

Then, the suction means can be connected to the top portion of the cannula 4.

Then, the surgeon can handle the positioning means 8, for making the blade 6 advance toward the side wall of the bed B formed in the cornea C, until the protruding tooth 61 thereof cuts the bottom edge of such wall for the required extension. In order to facilitate the surgeon in handling such positioning means 8, the latter could bear a "graduated" scale provided for the purpose. Moreover, such positioning could be carried out by temporarily connecting the dowel 8 to the abovementioned handling means.

At this point, the blade 6 lies in the abovementioned operative position. It will be understood that, during cutting, the blade 6 is held in said position by means for retaining implemented by the retaining tongue 81, the side surface 421 of the cannula 4, the protruding appendix 534 of the shaped body 5 and the side edges 532 of the latter.

Then, as shown in FIG. 2, the blade 6 can be actuated by the moving means 5, integrally to the positioning means 8, for carrying out an incision I at the bottom perimetric edge of the bed B. For an optimal housing of the donated portion, such incision I will have a radial extension preferably comprised in the range of about 0.3÷0.8 mm.

In particular, the shaped body 5 can be gripped at the actuation head 52 thereof and rotated about the cannula 4, and therefore with respect to the chassis 2, thereby causing the blade 6, guided by the conical portion 42, to follow a cutting motion of a substantially circular profile.

In the application taken into account here, the surgeon will perform a full 360 degrees rotation of said head 52, in order to have the incision I concern the entire bottom perimetric edge of the bed B.

Such incision I defines an overlap annular peripheral flap F. A sort of pocket is defined between the latter and the underlying corneal tissue, such pocket being apt to receive the donated corneal portion. In particular, the flap F can partially be overlapped to said donated portion, thereby easing the receiving thereof within the bed B and the transplant thereof onto the remaining part of the patient's cornea C.

It will presently be appreciated that the apparatus of the invention allows to simply and accurately carry out a corneal transplant, fully exploiting the advantages associated with the use of the excimer laser. In particular, the apparatus of the invention allows to carry out a corneal lamellar transplant, using the excimer laser to ablate a button of a thickness suiting the type and entity of the corneal lesion, a thickness not necessarily involving the full depth of the cornea C. Hence, the donated portion can optimally be housed and retained within the bed B by virtue of the pocket defined by said overlap flap F. Of course, all this entails reduced risks and convalescence times for the patient.

During the cutting, the visualization opening 521, which moves integrally to the blade 6, enables the surgeon to continuously visualize the blade itself.

Furthermore, it will be appreciated that the action of the counteracting spring 7 and the overall assembly of the member 11 with respect to the shaped body 5 allow the member 11 itself to axially lock the body 5 also when the latter rotates.

It will also be appreciated that the openings 521 and 522 allow a global lightening of the structure, reducing the load onto the patient's eyeball.

The part of the surgical intervention attaining the ablation of the donated corneal portion may be carried out with traditional techniques, or using an apparatus according to the invention.

It will be understood that the apparatus 1 of this first embodiment, by virtue of the reversible connection of the surgical device to the remaining components of the apparatus itself, may be provided to the user in a kit comprising several interchangeable surgical devices, e.g., one or more blades. Furthermore, in order to fit different diameters of the bed B, the apparatus may be provided with cannulas of different dimensions.

FIGS. 4 to 7 relate to a second and to a third embodiment of the invention. Such further embodiments will be disclosed only referring to the differences thereof with respect to the first embodiment, and analogous components will be indicated by the same reference number.

Figure 4:
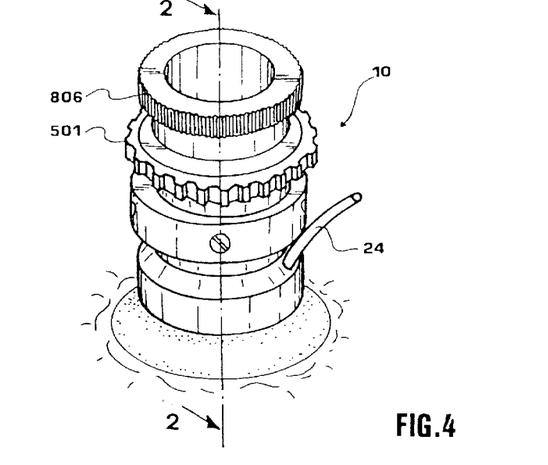
FIG. 4 relates to a second embodiment of the apparatus of the invention, showing a perspective view thereof.
Figure 5:
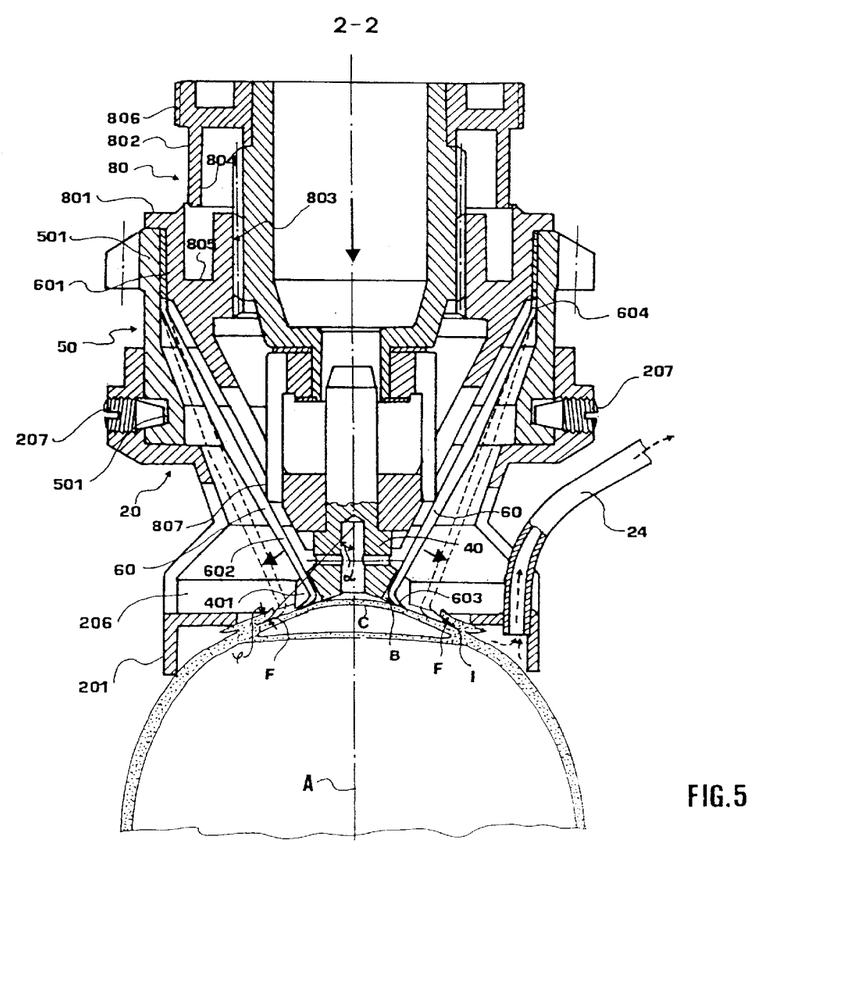
FIG. 5 is a sectional view of the apparatus of FIG. 4 taken along line B—B of the latter Figure, in an operative condition, during lamellar corneal transplant surgery.

With initial reference to FIGS. 4 and 5, in a second embodiment an apparatus according to the invention, in this case indicated with 10, comprises a chassis 20, apt to be placed onto the eyeball. The chassis 20 develops vertically, with substantially circular transverse sections, and it has several side windows 206, both for enabling the surgeon to visualize the operation site and for lightening the structure.

Bottomwise, the chassis 20 comprises an annular structure 201 analogous to that hereto disclosed with reference to the first embodiment, passed through suction ducts 24.

The apparatus 10 further comprises surgical device moving means 50. In this second embodiment, such means 50 comprises a shaped body, also indicated with 50, rotatably connected to the chassis 20. Such rotatable connection is carried out by pins 207, fixed with the chassis 20 and protruding internally thereto, received in a suitable track 511 of the shaped body 50.

Also in this second embodiment the shaped body 50 has an actuation head, indicated with 520, protruding topwise from the chassis 20. Such head 520 is apt to be actuated by the surgeon to generate a driving motion of substantially circular profile of two surgical devices, in particular two blades 60 apt to penetrate the corneal tissue.

The apparatus 10 further comprises, internally to the chassis 2, surgical device positioning means, globally indicated with 80, allowing also an adjustment of the relative position of the blades 60 with respect to the eyeball. Hence, such means 80 allows an adjustment of the depth and of the radial extension of the penetration of the blades. In the present embodiment, such means 80 comprises a first body 801, secured to the shaped body 50 at the actuation head 501 thereof, and a second body 802, sliding internally to the first body 801. In particular, these two bodies 801 and 802 are coupled by a screw-thread coupling 803. In this case as well, in the bottomwise translation motion of the second body 802 with respect to the first body 801 a safety stop is provided. Such stop is implemented by the abutment of a protruding annular abutting edge 804 of the second body 802 onto a corresponding annular groove 805 of the first body 801.

Topwise, the sliding body 802 comprises a handling head 806, which can be gripped by a surgeon for advancing or moving backward the sliding body. Bottomwise, the sliding body 802 has thrusting means 807, apt to bias on the above-mentioned blades 60 to retract themselves, as it will be further detailed hereinafter.

The apparatus 10 further comprises, bottomwise and in a centrated position, a housing 40 for said blades 60, apt to be rested onto the patient's cornea C. To this end, the device 40 is secured to the chassis 20, in a raised position with respect to the annular structure 201. The device 40 has two side openings 401, each apt to house a respective blade 60, as it will hereinafter be illustrated.

Each blade 60 has a top locking portion 601, locked between the actuation head 501 and the first body 801 of the positioning means 80. According to an embodiment variant, in this case as well such locking may be provided by a reversible engagement.

Each blade 60 further has an intermediate stem 602, slanting inwards with respect to the locking portion 601. Therefore, between such two portions a privileged strain region 604 of the blade 60 is defined. The stem 602 is mainly housed in an annular room defined between the chassis 20 and the sliding body 802.

Lastly, each blade 60 has a flat-bottomed end cutting portion 603. The cutting portion 603 has a thickness tapering according to a cutting-edge angle $\phi$, and it is slanting with respect to the stem 602.

The thrusting means 807 can press onto the stem 602 of each blade 60. As mentioned hereto, such means 807 are apt to retract the blades 60, causing an outwards rotation of the stem 602 and of the corresponding cutting portion 603 about said privileged strain region 604. The depth and the radial extension of the incision of the cornea C will be determined by the entity of the retraction of the blades 60.

Hereinafter, the operation modes of the apparatus 10 of the above-disclosed second embodiment will briefly be illustrated.

The apparatus 10 can be provided to the user in a fully assembled condition.

In this case as well, in order to carry out the surgery the application of an eyelid retractor and the use of the excimer laser for forming a bed B is provided. Then, the apparatus 10 may be placed onto the eyeball at the annular structure 201, and the suction ducts 24 connected to traditional suction devices.

In such configuration of rest onto the eyeball, the housing 40 is also placed onto the eyeball, and in particular within the bed B. Moreover, in this initial condition the thrusting means 807 are placed backwards, so that the protruding portions 603 of the blades 60 be completely housed within the respective room 401, hence being shielded thereby.

In order to carry out the cutting, the surgeon may actuate the thrusting means 807, by rotating the actuation head 806 of the sliding body 802, thereby causing a retraction of the blades 60 towards the side wall of the bed B of the desired entity. Once brought at the bottom perimetric edge of the bed B, the blades cut the cornea C transversely to the eyeball axis A. At the end of the retraction, the blades 60 lie in a desired operative position, wherein the cutting portions 63 thereof have a slant $\alpha$ with respect to the axis A of the eyeball depending on the entity of the retraction and on the overall shape and the arrangement of the blades themselves.

Concerning this latter aspect, it will be understood that the blades 60 are retained in the above-mentioned operative position by virtue of the locking thereof between the chassis 20 and the first body 801 and of the action of the thrusting means 807. Hence, all of these components implement surgical device retaining means.

Then, the surgeon can actuate the moving means 50 rotating the actuation head 501 thereof, thereby causing the rotation of the blades 60, integrally to the positioning means 80. Thus, onto the cornea C an incision I is carried out, according to an actuating path of a substantially circular profile. It will be understood that in this case the rotation angle of each blade 60 will be of about 180 degrees, in order to form, perimetrically to the bed B, an annular overlap flap F analogous to the one already disclosed with reference to the first embodiment.

Of course, alternative embodiments may provide a different number of blades, and therefore a different rotation angle of the moving means.

Compared to the first embodiment, the heretodisclosed apparatus 10 has the advantage of allowing, other conditions being equal, incisions of greater radial extension. In fact, during the penetration into the corneal tissue the cutting portion of the blades, by virtue of its flat bottom, is substantially parallel to the corneal profile, thus not risking to carry out an excessively deep cutting into the cornea itself when the radial extension of the incision increases. In particular, preferably such blades could carry out annular incisions of a diameter comprised in a range of about 6.5÷9.0 mm.

Figure 6:
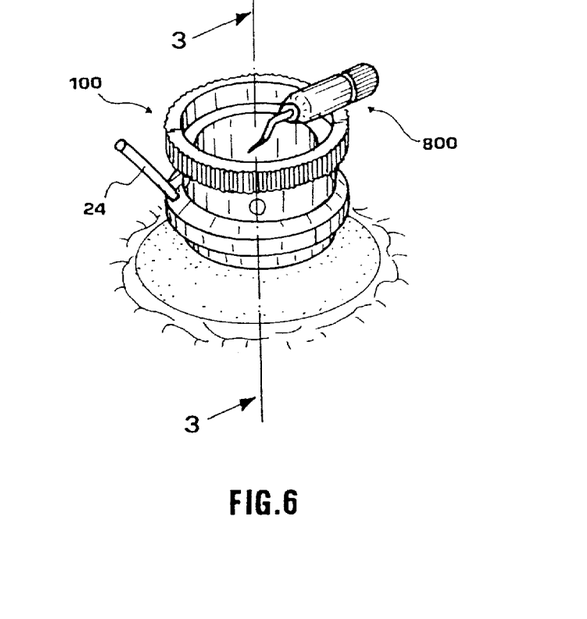
FIG. 6 relates to a third embodiment of the apparatus of the invention, showing a perspective view thereof.
Figure 7:
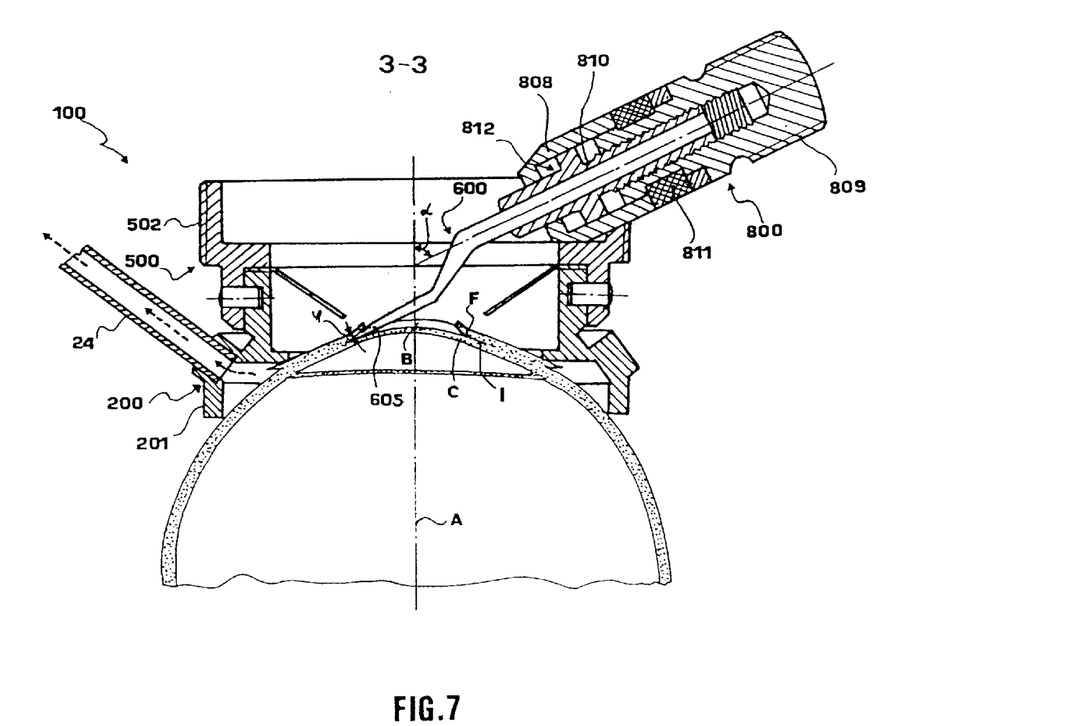
FIG. 7 is a sectional view of the apparatus of FIG. 6 taken along line C—C of the latter Figure, in an operative condition, during lamellar corneal transplant surgery.

With reference now to FIGS. 6 and 7, an apparatus for corneal surgery of a third embodiment, in particular a cutting apparatus, is globally indicated with 100. Such apparatus 100 provides a chassis 200 that develops vertically according to substantially circular sections. The chassis 200 comprises an annular structure 201 analogous to those already described with reference to the first two embodiments disclosed.

Topwise to such structure 201, the chassis 200 is rotatably connected to surgical device moving means 500, according to connection modes substantially analogous to those of the second embodiment. In this case as well, the surgical device is a blade 600 apt to penetrate the corneal tissue.

The moving means 500 is a shaped body, it also developing vertically, above the chassis 200, according to substantially circular sections. In this case as well, the moving means has an actuation head 502, apt to be gripped by a surgeon. In particular, such actuation head 502 has a substantially annular structure.

To the drive head 502, surgical device positioning means 800, also enabling an adjustment of the position of the blade 600 with respect to the eyeball, and therefore of the depth and extension of penetration thereof, are secured.

In this embodiment, the positioning means 800 comprises a substantially tubular case 808, welded to the actuation head 502.

The means 800 further comprises a handling head 809, rotatably connected to the case 808 and partially inserted therein. The axial translation of the handling head 809 with respect to the case 808 is prevented by an abutment ring 811 integral thereto, it also rotatably connected to the case 808.

Bottomwise, the handling head 809 bears an internal thread. This is engaged by a corresponding external thread of a plug 810, partially housed inside the case 808, within which said blade 600 is axially locked.

In this third embodiment as well, safety stop means, globally indicated with 812, for limiting the entity of the excursion of the translation of the plug 810 with respect to the case 808, i.e. the entity of the advancement of the blade 600, are provided. Such means 812 comprise respective annular abutting edges of the plug 810 and of the case 808.

The blade 600 has, externally to the plug 810, a shaped stem, for allowing the incision of the patient's cornea C. Such blade 600 ends in a cutting portion 605 of tapering thickness, having a cutting-edge angle $\phi$.

As it will be understood, in order to bring the blade 600 in a desired operative position, the surgeon can manipulate the positioning means 800 at the ring 811 thereof. By rotating such ring 811, the plug 810, and therefore the blade 600 integral thereto, are induced to translate with respect to the case 808, nearing to the side wall of a pre-formed bed B.

After such translation, the blade 600 cuts the cornea C, at the bottom perimetric edge of the bed B, for the desired extension. Upon reaching a desired operative position, the surgeon can actuate the blade 600, integrally to the positioning means 800, by the moving means 500, acting on the actuation head 502 of the latter. Thus, an incision I defining an overlap annular peripheral flap F is obtained.

In this case as well, in the operative position the blade 600 has a slant $\alpha$ with respect to the axis A of the eyeball.

It will be understood that alternative embodiments may provide a different blade profile and/or shape, depending upon the desired profile for the cutting of the bed and/or of the button.

Moreover, for the moving means embodiments alternative to the above-disclosed may provide kinematic motions different from the above-disclosed ones, apt to generate an actuating motion, e.g., a cutting motion, of a pre-set profile.

Further, alternative embodiments may provide the presence of position sensors arranged onto the surgical device, onto the positioning means and/or onto the moving means.

Those skilled in the art will understand that the apparatus of the invention, although designed to be used in the field of corneal transplant surgery, can advantageously be used to carry out keratoplastic or keratectomy surgery.

Further, it will be understood that, in the field of corneal transplant surgery, the above-mentioned pocket is apt to house donated, as well as synthetic, lenticular transplants.

Finally, it will be understood that, although the invention has hereto been described with reference to a surgical cutting device, in particular a blade, the apparatus of the invention can also advantageously incorporate different surgical devices.

From the above description it will be also understood that the invention also provides a surgical method for performing a corneal transplant, comprising the steps of:

forming a bed B of a desired thickness into the patient's cornea C, for example by excimer laser;

penetrating the side wall of the bed for a desired extension by one or more cutting tools, e.g. the blades described above, according to a penetration direction transverse to an eyeball axis A;

cutting an incision I, by said cutting tool, of a substantially circular profile so that a flap F of corneal tissue is obtained, a pocket being defined between the flap F and the underlying cornea; and resting a corneal portion, e.g. a donated corneal portion, to be transplanted into the bed B, so that the flap F partially overlaps it.

In particular, as shown with reference to the surgical apparatus of the invention, preferably the cutting tool penetrates the bed side wall at a bottom perimetral edge thereof for an extension of penetration comprised in a range of about 0.3÷0.8 mm.

Always according to a preferred embodiment, incision I has a diameter comprised in a range of about 6.5÷9.0 mm.

The present invention has hereto been disclosed with reference to preferred embodiments thereof. It is understood that there may be other embodiments related to the same inventive core, all falling within the protective scope of the claims disclosed hereinafter.

What is claimed is:

1. An apparatus for corneal surgery, comprising:
   a chassis, apt to be placed onto the eyeball for centrating said apparatus with respect to the eyeball;
   at least one surgical device, apt to operate onto corneal tissue, insertable in said apparatus;
   surgical device positioning means, movable with respect to said chassis, apt to be handled by a user for bringing said at least one surgical device in an operative position;
   surgical device moving means, rotatable with respect to said chassis, apt to be handled by the user for actuating said at least one surgical device, in said operative position, according to a pre-set actuating path, which actuating path has a substantially circular profile; and
   a conical surgical device guide, integral to said chassis, apt to be placed onto the cornea and having a conical side wall apt to guide said surgical device in said actuating path.

2. The apparatus according to claim 1, wherein said surgical device comprises a blade.

3. The apparatus according to claim 1, wherein said operative position provides said surgical device to have a slant with respect to the eyeball axis.

4. The apparatus according to claim 3, wherein said positioning means provides a slanting arrangement with respect to a longitudinal axis of said apparatus.

5. The apparatus according to claim 1, wherein the arrangement of said positioning means is such that said means are moved by said moving means, said movement being integral with that of said surgical device.

6. The apparatus according to claim 1, wherein said positioning means comprises a system for adjusting the position of said surgical device with respect to the eyeball.

7. The apparatus according to claim 1, wherein said surgical device guide is apt to be connected to suction means.

8. The apparatus according to claim 1, comprising axial locking means, for axially locking said moving means with respect to said surgical device guide.

9. The apparatus according to claim 8, wherein said axial locking means comprises an elastic member, housed within said moving means, and a locking member, apt to abut on said elastic member.

10. The apparatus according to claim 1, comprising means for reversibly engaging said surgical device to said positioning means.

11. The apparatus according to claim 1, comprising a safety stop of said positioning means.

12. The apparatus according to claim 1, wherein said moving means comprises an actuation head, apt to be gripped by the user.

13. The apparatus according to claim 12, wherein visualization opening is formed on said actuation head for enabling the user to visualize said surgical device.

14. The apparatus according to claim 1, having a disassemblable modular structure.

15. The apparatus according to claim 1, wherein said chassis is disassemblable.

16. A corneal surgery kit, comprising an apparatus according to claim 1 and a plurality of interchangeable surgical devices.

17. An apparatus for corneal surgery, comprising:
- a chassis, apt to be placed onto the eyeball for centrating said apparatus with respect to the eyeball;
- at least one surgical device, apt to operate onto corneal tissue, insertable in said apparatus;
- surgical device positioning means, movable with respect to said chassis, apt to be handled by a user for bringing said at least one surgical device in an operative position;
- surgical device moving means, rotatable with respect to said chassis, apt to be handled by the user for actuating said at least one surgical device, in said operative position, according to a pre-set actuating path, which actuating path has a substantially circular profile; and
- a conical surgical device guide, integral to said chassis, apt to be placed onto the cornea and having a conical side wall apt to guide said surgical device in said actuating path, wherein the arrangement of said positioning means is such that said means are moved by said moving means, said movement being integral with that of said surgical device, said positioning means comprises a system for adjusting the position of said surgical device with respect to the eyeball and wherein said system for adjusting comprises a screw-thread coupling between said positioning means and said moving means.

* * * * *